(12) United States Patent
Kuechler et al.

(10) Patent No.: US 9,365,467 B2
(45) Date of Patent: Jun. 14, 2016

(54) PROCESS OF PRODUCING CYCLOHEXYLBENZENE

(75) Inventors: Keith H. Kuechler, Friendswood, TX (US); James R. Lattner, LaPorte, TX (US); Christopher L. Becker, Manhattan, KS (US); Jihad M. Dakka, Whitehouse Station, NJ (US); Tan-Jen Chen, Kingwood, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 322 days.

(21) Appl. No.: 13/883,742

(22) PCT Filed: Dec. 2, 2011

(86) PCT No.: PCT/US2011/063119
§ 371 (c)(1),
(2), (4) Date: Aug. 16, 2013

(87) PCT Pub. No.: WO2012/082409
PCT Pub. Date: Jun. 21, 2012

(65) Prior Publication Data
US 2014/0371498 A1    Dec. 18, 2014

Related U.S. Application Data

(60) Provisional application No. 61/468,298, filed on Mar. 28, 2011, provisional application No. 61/424,242, filed on Dec. 17, 2010.

(51) Int. Cl.
*C07C 2/74*    (2006.01)
*C07C 5/367*   (2006.01)
(Continued)

(52) U.S. Cl.
CPC . *C07C 2/74* (2013.01); *C07C 5/367* (2013.01); *C07C 6/126* (2013.01);
(Continued)

(58) Field of Classification Search
None
See application file for complete search history.

(56) References Cited

U.S. PATENT DOCUMENTS 3,784,619 A    1/1974   Crone, Jr. et al.
3,962,362 A *  6/1976   Suggitt ............... 585/252
(Continued)

FOREIGN PATENT DOCUMENTS

EP      0 293 032      11/1988
TW      201138956      11/2011
(Continued)

OTHER PUBLICATIONS

U.S. Appl. No. 61/424,242 entitled, "*Dehydrogenation Catalyst and Process*", filed Dec. 17, 2010.
(Continued)

*Primary Examiner* — In Suk Bullock
*Assistant Examiner* — Philip Louie
(74) *Attorney, Agent, or Firm* — Stephen A. Baehl (57) ABSTRACT

In a process for producing cyclohexylbenzene, benzene is contacted with hydrogen under hydroalkylation conditions effective to form a first effluent stream comprising cyclohexylbenzene, cyclohexane, methylcyclopentane, and unreacted benzene. At least a portion of the first effluent stream is contacted with a dehydrogenation catalyst under dehydrogenation conditions to convert at least a portion of the cyclohexane to benzene thereby forming a second effluent stream. The amount of methylcyclopentane in the second effluent stream is different by no more than 65% of the total amount of the portion of the first effluent stream, said amounts being on a weight basis. A methylcyclopentane-containing stream is removed from either the first or the second effluent stream and at least a portion of the second effluent stream containing benzene is recycled to the hydroalkylation step.

14 Claims, 5 Drawing Sheets

(51) Int. Cl.
*C07C 6/08* (2006.01)
*C07C 6/12* (2006.01)

(52) U.S. Cl.
CPC ........ *C07C 2101/08* (2013.01); *C07C 2101/14* (2013.01); *C07C 2521/08* (2013.01); *C07C 2523/14* (2013.01); *C07C 2523/42* (2013.01)

(56) References Cited

U.S. PATENT DOCUMENTS

| | | | |
|---|---|---|---|
| 4,094,918 | A | 6/1978 | Murtha et al. |
| 4,122,125 | A | 10/1978 | Murtha et al. |
| 4,177,165 | A | 12/1979 | Murtha et al. |
| 4,206,082 | A | 6/1980 | Murtha et al. |
| 4,439,409 | A | 3/1984 | Puppe et al. |
| 4,826,667 | A | 5/1989 | Zones et al. |
| 4,954,325 | A | 9/1990 | Rubin et al. |
| 5,053,571 | A | 10/1991 | Makkee |
| 5,236,575 | A | 8/1993 | Bennett et al. |
| 5,250,277 | A | 10/1993 | Kresge et al. |
| 5,362,697 | A | 11/1994 | Fung et al. |
| 6,014,018 | A | 1/2000 | Wu et al. |
| 6,037,513 | A | 3/2000 | Chang et al. |
| 6,077,498 | A | 6/2000 | Diaz Cabañas et al. |
| 6,720,462 | B2 | 4/2004 | Kuhnle et al. |
| 6,756,030 | B1 | 6/2004 | Rohde et al. |
| 7,579,511 | B1 * | 8/2009 | Dakka et al. ............ 585/316 |
| 2011/0015457 | A1 | 1/2011 | Cheng et al. |

FOREIGN PATENT DOCUMENTS

| | | |
|---|---|---|
| WO | WO 97/17290 | 5/1997 |
| WO | WO 2007/084440 | 7/2007 |
| WO | WO 2009/025939 | 2/2009 |
| WO | 2009/128984 | 10/2009 |
| WO | WO 2009/131769 | 10/2009 |
| WO | WO 2010/042142 | 4/2010 |
| WO | WO 2011/096991 | 8/2011 |

OTHER PUBLICATIONS

U.S. Appl. No. 61/468,298 entitled, "*Dehydrogenation Process*", filed Mar. 28, 2011.

* cited by examiner

PROCESS OF PRODUCING CYCLOHEXYLBENZENE

PRIORITY CLAIM

This application is a National Stage Application of International Application No. PCT/US2011/063119 filed Dec. 2, 2011, which claims priority to U.S. Provisional Application Ser. No. 61/424,242 filed Dec. 17, 2010 and U.S. Provisional Application Ser. No. 61/468,298 filed Mar. 28, 2011, the disclosures of which are fully incorporated herein by their reference.

CROSS REFERENCE TO RELATED PATENT APPLICATIONS

This application is related to U.S. Provisional Application Ser. No. 61/424,242 filed Dec. 17, 2010 (2010EM305); U.S. Provisional Application Ser. No. 61/468,298 filed Mar. 28, 2011 (2011EM082); US Publication No. 2011/0015457; and U.S. Pat. No. 7,579,511.

FIELD

The present invention relates to a process for producing cyclohexylbenzene and to the use of the resultant cyclohexylbenzene in the production of phenol and cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide, and then cleavage of the hydroperoxide to produce equimolar amounts of phenol and acetone. However, the world demand for phenol is growing more rapidly than that for acetone. In addition, due to a developing shortage, the cost of propylene is likely to increase. Thus, a process that uses higher alkenes instead of propylene as feed and co-produces higher ketones, rather than acetone, may be an attractive alternative route to the production of phenols.

One such process proceeds via cyclohexylbenzene, followed by the oxidation of the cyclohexylbenzene to cyclohexylbenzene hydroperoxide, which is then cleaved to produce phenol and cyclohexanone in substantially equimolar amounts.

Cyclohexylbenzene can be produced from benzene by the process of hydroalkylation or reductive alkylation. In this process, benzene is heated with hydrogen in the presence of a catalyst such that the benzene undergoes partial hydrogenation to produce a reaction intermediate such as cyclohexene which then alkylates the benzene starting material. Thus, U.S. Pat. Nos. 4,094,918 and 4,177,165 disclose hydroalkylation of aromatic hydrocarbons over catalysts which comprise nickel-treated and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffer from the problems that the selectivity to cyclohexylbenzene is low, particularly at economically viable benzene conversion rates, and that large quantities of unwanted by-products are produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt and mixtures thereof, and the contacting step is conducted at a temperature of 50° C. to 350° C., a pressure of 100 kPa to 7000 kPa, a benzene to hydrogen molar ratio of 0.01 to 100 and a weight hourly space velocity (WHSV) of 0.01 hr$^{-1}$ to 100 hr$^{-1}$. The '513 patent discloses that the resultant cyclohexylbenzene can then be oxidized to the corresponding hydroperoxide and the peroxide decomposed to the desired phenol and cyclohexanone.

Although the process of the '513 patent represents a significant improvement over earlier processes for the hydroalkylation of benzene, it still suffers from the problem that significant quantities of impurities, particularly cyclohexane and methylcyclopentane, are produced in addition to the desired cyclohexylbenzene. These impurities represent loss of valuable benzene feed. Moreover, unless removed, these impurities will tend to build up in the benzene recycle stream thereby displacing benzene and further increasing the production of undesirable by-products.

One potential solution to this problem is proposed in U.S. Pat. No. 7,579,511, which describes a process for making cyclohexylbenzene in which benzene undergoes hydroalkylation in the presence of a first catalyst to form a first effluent composition containing cyclohexylbenzene, cyclohexane, methylcyclopentane, and unreacted benzene. The first effluent composition is then separated into a cyclohexane/methylcyclopentane-rich composition, a benzene-rich composition, and a cyclohexylbenzene-rich composition and the cyclohexane/methylcyclopentane-rich composition is contacted with a second, low acidity, dehydrogenation catalyst to convert at least a portion of the cyclohexane to benzene and at least a portion of the methylcyclopentane to linear and/or branched paraffins and form a second effluent composition. The benzene-rich composition and the second effluent composition can then be recycled to the hydroalkylation step.

Another solution is proposed in International Patent Publication No. WO2009/131769, in which benzene undergoes hydroalkylation in the presence of a first catalyst to produce a first effluent composition containing cyclohexylbenzene, cyclohexane, and unreacted benzene. The first effluent composition is then divided into a cyclohexylbenzene-rich composition and a $C_6$ product composition comprising cyclohexane and benzene. At least a portion of the $C_6$ product composition is then contacted with a dehydrogenation catalyst under dehydrogenation conditions to convert at least a portion of the cyclohexane to benzene and produce a second effluent composition which comprises benzene and hydrogen and which can be recycled to the hydroalkylation step.

Both of the processes disclosed in U.S. Pat. No. 7,579,511 and WO2009/131769 rely on the use of a dehydrogenation catalyst comprising a Group VIII metal on a porous inorganic support such as aluminum oxide, silicon oxide, titanium oxide, zirconium oxide, activated carbon, and combinations thereof. However, the conditions that favor methylcyclopentane conversion also favor isomerization of the more prevalent cyclohexane to methylcyclopentane. Moreover, the methylcyclopentane normally converts to acyclic paraffins, such as n-hexane, which forms an azeotrope with benzene making it no easier to separate from the effluent than the methylcyclopentane. Finally, methylcyclopentane has a considerably higher octane value than its acyclic paraffin conversion products, making it more valuable to recover the methylcyclopentane as a motor gasoline blendstock rather than consume valuable hydrogen in its dehydrogenation.

There is therefore a need for an improved process for reducing the build-up of methylcyclopentane in the benzene recycle streams present in benzene hydroalkylation processes.

SUMMARY

Accordingly, the invention relates in one aspect to a process for producing cyclohexylbenzene, (a) contacting benzene and hydrogen under hydroalkylation conditions effective to form a first effluent stream comprising cyclohexylbenzene, cyclohexane, methylcyclopentane, and unreacted benzene;

(b) contacting at least a portion of the first effluent stream with a dehydrogenation catalyst under dehydrogenation conditions to convert at least a portion of the cyclohexane to benzene thereby forming a second effluent stream, wherein the amount of methylcyclopentane in the second effluent stream is different by no more than 65% of the total amount of the portion of the first effluent stream, said amounts being on a weight basis;

(c) removing a methylcyclopentane-containing stream from either the first effluent stream or the second effluent stream; and (d) recycling at least a portion of the second effluent stream containing benzene to (a).

Conveniently, a cyclohexylbenzene-containing stream is recovered from said first effluent stream prior to said contacting (b), such as by fractionation.

Conveniently, the contacting step (b) is conducted in the presence of a dehydrogenation catalyst comprising 0.05 wt % to 0.5 wt % of a metal selected from Group 14 of the Periodic Table of Elements; and 0.1 wt % to 2 wt % of a metal selected from Groups 6 to 10 of the Periodic Table of Elements, the wt % s being based upon total weight of the first catalyst. In one embodiment, the metal selected from Group 14 of the Periodic Table of Elements comprises tin and the metal selected from Groups 6 to 10 of the Periodic Table of Elements comprises platinum and/or palladium.

Conveniently, the contacting step (b) is conducted at dehydrogenation conditions comprising a temperature between 200° C. and 550° C. and a pressure between 100 kPa and 7,000 kPa.

Conveniently, the methylcyclopentane-containing stream is removed from either the first or the second effluent stream by fractionation.

Conveniently, the methylcyclopentane-containing stream contains from about 5 wt % to about 50 wt % methylcyclopentane, from about 5 wt % to about 50 wt % cyclohexane and/or from about 10 wt % to about 80 wt % benzene, the wt % s based upon the weight of the methylcyclopentane-containing stream.

Conveniently, the second effluent stream portion contains from about 0.1 wt % to about 5 wt % methylcyclopentane, from about 0.1 wt % to about 1 wt % methylcyclopentane and/or from about 0.1 wt % to about 10 wt % cyclohexane, the wt % s based upon the weight of the second effluent stream portion.

The invention also relates to a process comprising:

(a) contacting benzene and hydrogen in the presence of a hydroalkylation catalyst under hydroalkylation conditions effective to form a first effluent stream comprising cyclohexylbenzene, methylcyclopentane, and unreacted benzene;

(b) supplying at least a portion of said first effluent stream to a fractionation system to recover a first product stream containing cyclohexylbenzene and a second product stream containing from about 1 wt % to about 99 wt % of the methylcyclopentane contained in said first effluent stream portion and leave a benzene-containing stream containing up to 5 wt % methylcyclopentane; and (c) recycling at least a portion of the benzene-containing stream to (a).

Conveniently, the second product stream contains from about 2 wt % to about 80 wt %, of the methylcyclopentane contained in said first effluent stream portion.

Conveniently, the second product stream contains from about 5 wt % to about 50 wt % methylcyclopentane and from about 10 wt % to about 80 wt % benzene, the wt % based upon the weight of the second product stream.

Conveniently, the benzene-containing stream contains from about 0.1 wt % to about 1 wt % methylcyclopentane, the wt % based upon the weight of the benzene-containing stream.

The invention also relates to a process comprising:

(a) contacting dicyclohexylbenzene and benzene in the presence of a transalkylation catalyst under transalkylation conditions effective to form a transalkylation effluent stream comprising cyclohexylbenzene, methylcyclopentane, and unreacted benzene;

(b) supplying at least a portion of said transalkylation effluent stream to a fractionation system to recover a first product stream containing cyclohexylbenzene and a second product stream containing from about 1 wt % to about 99 wt % of the methylcyclopentane contained in said first effluent stream portion and leave a benzene-containing stream containing up to 5 wt % methylcyclopentane; and (c) recycling at least a portion of the benzene-containing stream to (a) or to a benzene hydroalkylation process.

The invention also relates to a process comprising:

(a) contacting benzene and hydrogen under hydroalkylation conditions effective to form a first effluent stream comprising cyclohexylbenzene, cyclohexane, methylcyclopentane, and unreacted benzene;

(b) contacting at least a portion of the first effluent stream with a dehydrogenation catalyst under dehydrogenation conditions sufficient to convert at least a portion of the cyclohexane in the first effluent stream portion to benzene and form a second effluent stream, wherein less than 10% of the methylcyclopentane in the second effluent stream is converted to a paraffin on a weight basis;

(c) removing a methylcyclopentane-containing stream from either the first effluent stream or the second effluent stream; and (d) recycling at least a portion of the second effluent stream containing benzene to (a).

DETAILED DESCRIPTION OF THE EMBODIMENTS

Described herein is a process for reducing the level of methylcyclopentane in the reaction effluent from the production of cyclohexylbenzene by the hydroalkylation of benzene. Even using a selective catalyst, such as an MCM-22 family zeolite, the hydroalkylation of benzene produces a number of byproducts in addition to the desired cyclohexylbenzene. A prevalent byproduct is cyclohexane, which is typically produced in a selectivity from about 1 wt % to about 20 wt % of the converted benzene feed, but which can be returned to useful benzene by dehydrogenation. Methylcyclopentane is another significant impurity, which is typically produced in a selectivity from about 0.01 wt % to about 1 wt % of the converted benzene feed. Methylcyclopentane forms an azeotrope with benzene, but only at a benzene concentration of about 12 wt % and this azeotrope boils at 78° C., which is 7° C. higher than the cyclohexane/benzene azeotrope having a benzene concentration of about 52 wt %.

In present process, at least some of the methylcyclopentane by-product of the hydroalkylation reaction or the hydrogenation reaction is recovered, normally by fractional distillation. The methylcyclopentane can be recovered directly from the $C_6$ fraction of the hydroalkylation reaction effluent. More preferably, the methylcyclopentane is recovered after the $C_6$ fraction is subjected to dehydrogenation arranged to convert at least a portion of the cyclohexane in the $C_6$ fraction to benzene, with the proviso that the amount of methylcyclopentane is changed by no more than 65% of the total amount of the $C_6$ fraction subjected to dehydrogenation, said amounts on a weight basis. In this way, the loss of cyclohexane by isomerization during the dehydrogenation can be kept to a minimum, whereas, although the recovered methylcyclopentane will inevitably contain some benzene, the total amount of benzene removed from the system with the methylcyclopentane is relatively small. The recovered methylcyclopentane can be used as a motor gasoline blendstock.

In one preferred embodiment, the present process forms part of an integrated process for producing phenol from benzene in which the cyclohexylbenzene produced in the benzene hydroalkylation reaction is oxidized to produce cyclohexylbenzene hydroperoxide and the hydroperoxide is cleaved to produce phenol and cyclohexanone. The ensuing description will therefore focus on this integrated process.

Production of the Cyclohexylbenzene

The initial step of the integrated process for producing phenol is the selective hydrogenation of benzene in the presence of a bifunctional hydroalkylation catalyst. The hydroalkylation reaction produces cyclohexylbenzene (CHB) according to the following reaction:

Any commercially available benzene feed can be used in the hydroalkylation reaction, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 wt % and about 10 wt %, such as between about 0.1 wt % and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Treatment of the Cyclohexylbenzene Product

Although the hydroalkylation reaction using an MCM-22 family zeolite catalyst is highly selective towards cyclohexylbenzene, the hydroalkylation reaction will inevitably produce certain by-products. As stated previously, a prevalent by-product is normally cyclohexane but generally the reaction effluent will also contain dicyclohexylbenzene, tri-cyclobenzene and even heavier alkylates, and methylcyclopentane. Methylcyclopentane is also generated in the transalkylation reaction described in more detail below.

The hydroalkylation reaction effluent is normally fractionated to separate the effluent into one or more $C_6$ fractions containing most of the unreacted benzene and most of the cyclohexane and methylcyclopentane by-products, a $C_{12}$ fraction containing most of the cyclohexylbenzene product, and a $C_{18}$ fraction containing most of the dicyclohexylbenzene by-product, and possibly a $C_{24}$ or higher product heavy alkylate byproduct. As used herein, "unreacted benzene" means the benzene that does not react in the hydroalkylation reaction.

In one embodiment, the fractionation of the hydroalkylation reaction effluent produces a $C_6$ fraction and this $C_6$ fraction is then contacted with a dehydrogenation catalyst under dehydrogenation conditions sufficient to convert at least a portion of the cyclohexane in the $C_6$ fraction to benzene but changes the amount of methylcyclopentane by no more than 65%, (or 30%, or 10% or 7.0%, or 5.0%, or 2.0%, or 1.0%, or 0.7%, or 0.5%, or 0.2%, or 0.1%) of the total amount of the $C_6$ fraction contacted with the dehydrogenation catalyst, said amounts on a weight basis. Generally the dehydrogenation is arranged to convert at least 25 wt %, such at least 50 wt %, for example at least 90 wt % of the cyclohexane in the $C_6$ fraction to benzene but to change the amount of methylcyclopentane by no more than 5 wt %, such as no more than 2 wt %, or no more than 1 wt %, or no more than 0.5 wt %, or no more than 0.1 wt % of the total amount of the $C_6$ fraction contacted with the dehydrogenation catalyst.

In various embodiments, the amount of methylcyclopentane in the $C_6$ fraction is changed by no more than 65% (or 30%, or 10%, or 7.0%, or 5.0%, or 2.0%, or 1.0%, or 0.7%, or 0.5%, or 0.2%, or 0.1%) of the total amount of the $C_6$ fraction contacted with the dehydrogenation catalyst. This amount is with regard to weight, or weight rate (per unit time). In the event that one or more For example, in an embodiment in which the amount of methylcyclopentane in the C6 fraction is changed by no more than 10% of the total amount of the C6 fraction contacted with the dehydrogenation catalyst, and the total rate of the $C_6$ fraction contacted with the dehydrogenation catalyst is 100 lb/hr, the rate of methylcyclopentane in the effluent may be no more or less than 10 lb/hr different than that found in the $C_6$ fraction. By further example, if the rate of methylcyclopentane in the $C_6$ fraction were 15 lb/hr of the total 100 lb/hr, the amount of methylcyclopentane rate in the effluent is no less than 5 lb/hr and no greater than 25 lb/hr. By further example, if the rate of methylcyclopentane in the $C_6$ fraction were 5 lb/hr of the total 100 lb/hr, the amount of methylcyclopentane rate in the effluent is no less than 0 lb/hr and no greater than 15 lb/hr.

There may or may not be any methylcyclopentane in the $C_6$ fraction contacted with the dehydrogenation catalyst, and yet it may be present in the effluent. For example, with certain dehydrogenation catalysts and under certain dehydrogenation conditions, methylcyclopentane may be created via the isomerization of cyclohexane, even if no methylcyclopentane was initially present.

In various embodiments, the amount of methylcyclopentane in the effluent stream may be the same as the amount of the $C_6$ fraction contacted with the dehydrogenation catalyst, i.e., there is no change within the accuracy of the analytical tools used to measure.

In various embodiments, the dehydrogenation catalyst employed in the dehydrogenation reaction comprises (i) a metal selected from Group 14 of the Periodic Table of Elements; and (ii) a metal selected from Groups 6 to 10 of the Periodic Table of Elements, the wt % s based upon total weight of the dehydrogenation catalyst. As used herein, the numbering scheme for the Periodic Table Groups disclosed herein is the New Notation provided on the inside cover of *Hawley's Condensed Chemical Dictionary* (14th Edition), by Richard J. Lewis.

Generally, the Group 14 metal is present in the dehydrogenation catalyst in an amount of at least 0.05 wt %, at least 0.1 wt %, at least 0.15 wt %, at least 0.2 wt %, at least 0.3 wt %, at least 0.4 wt %, or at least 0.5 wt %, or at least 1 wt %, or at least 5 wt % based upon total weight of the dehydrogenation catalyst. In one embodiment, the Group 14 metal is tin. In various embodiments, the Group 14 is present in an amount between 0.05 wt % and 5 wt %, or 0.05 wt % and 1 wt %, or 0.05 wt % and 0.5 wt % of the catalyst or between 0.1 wt % and 0.4 wt % of the catalyst or between 0.1 wt % and 0.3 wt %, or between about 0.15 wt % and 0.2 wt % of the dehydrogenation catalyst.

In addition, the dehydrogenation catalyst may comprise a metal selected from Groups 6 to 10 of the Periodic Table of Elements, such as platinum and/or palladium. Typically, the metal selected from Groups 6 to 10 of the Periodic Table of Elements is present in an amount between 0.05 and 10 wt % of the catalyst, such as between 0.1 wt % and 5 wt % of the catalyst or between 0.2 wt % and 2 wt % of the catalyst. In another embodiment, the Group 6 to 10 metal is present in an amount of at least 0.1 wt %, at least 0.2 wt %, at least 0.3 wt %, at least 0.4 wt %, at least 0.5 wt %, at least 0.6 wt %, at least 0.7 wt %, at least 0.8 wt %, at least 0.9 wt %, or at least 1.0 wt %. In various embodiments, the Group 6-10 metal is present in an amount between 0.1 wt % and 5 wt % of the catalyst, or between 0.1 wt % and 3 wt % of the catalyst, or between 0.1 wt % and 2 wt % of the catalyst, or between about 0.15 wt % and 1.5 wt % of the catalyst.

In various embodiments, the catalyst composition comprises less than 2 wt % of nickel, or <1 wt % nickel, or <0.5 wt % nickel, or less than 0.1 wt % nickel, or no nickel. In various embodiments, the catalyst composition comprises less than 2 wt % of cobalt, or <1 wt % cobalt, or <0.5 wt % cobalt, or less than 0.1 wt % cobalt, or no cobalt. In various embodiments, the catalyst composition is free, or substantially free, of ruthenium, rhodium, lead, and/or germanium, and/or other active elemental components.

In various embodiments, the ratio of the metal selected from Groups 6 to 10 of the Periodic Table of Elements to the metal selected from Group 14 of the Periodic Table of Elements (e.g., the Pt/Sn ratio) in the catalyst is greater than 0.5, or greater than 1, or greater than 1.5, or greater than 2.5, or greater than 2.7, or greater than 3, with a ratio of greater than 2.5 to 400, or 2.7 to 200, or 3 to 100 being preferred.

In various embodiments, the dehydrogenation catalyst further comprises a support. Conveniently, the dehydrogenation catalyst support is selected from the group consisting of silica, alumina, a silicate, an aluminosilicate, zirconia, carbon or carbon nanotubes. In various embodiments, the support comprises an inorganic oxide such as one or more of silicon dioxide, titanium dioxide, and zirconium dioxide. The support may or may not comprise a binder. Impurities that can be present in the catalyst support are, for example, sodium salts such as sodium silicate which can be present from anywhere from 0.01 wt % to 2 wt %. Suitable silica supports are described in, for example, PCT Pub. No. WO/2007084440A1 filed on Jan. 12, 2007, and entitled "Silica Carriers" and is hereby incorporated by reference for this purpose.

It will be understood that the metal selected from Group 14 and/or the metal selected from Groups 6 to 10 of the Periodic Table of Elements may not be purely the elemental metal, but could, for example, be at least partly in another form, such as a salt, oxide, chloride, hydride, sulfide, carbonate, etc. For purposes of this application, the wt % of metal in the catalyst composition is calculated based upon the amount of metal used to form the component in the catalyst composition. Moreover, for purposes of determining wt % s of various components of the dehydrogenation catalyst, only that portion of the support that supports the Group 14 metal and/or the Group 6-10 metal is considered. For example, a catalyst composition made with 1.9 grams of tin chloride salt (1 gram of tin) and 22.29 grams of tetraamine platinum hydroxide solution (4.486 wt % Pt) that is supported on 98 grams of silicon dioxide contains 1 wt % of tin and 1 wt % Pt, based upon total weight of the catalyst composition.

Suitable dehydrogenation conditions include a temperature of about 250° C. to about 500° C., a pressure of about 100 kPa to 7000 kPa, a weight hourly space velocity of about 0.2 hr$^1$ to 50 hr$^1$, and a hydrogen to hydrocarbon feed molar ratio of about 0 to about 20.

After removal of the hydrogen, the dehydrogenation effluent typically contains at least 25 wt %, such at least 50 wt %, for example at least 90 wt % benzene, from about 0.1 wt % to about 10 wt %, such as from about 1 wt % to about 5 wt %, cyclohexane and from about 0.1 wt % to about 5 wt %, such as from about 0.5 wt % to about 1 wt %, methylcyclopentane. The dehydrogenation effluent may then be fractionated to produce a major fraction rich in benzene and a minor fraction rich in methylcyclopentane. The benzene-rich fraction typically comprises from about 90 wt % to about 99 wt % of the liquid dehydrogenation effluent and contains no more than 5 wt %, normally at least 0.01 wt %, such as about 0.1 to about 1 wt %, methylcyclopentane, possibly no detectable methylcyclopentane, and from about 0.1 wt % to about 10 wt % cyclohexane, such as from about 0.5 to about 5 wt % cyclohexane. The methylcyclopentane-rich fraction typically comprises from about 1 wt % to about 10 wt % of the liquid dehydrogenation effluent and contains from about 5 wt % to about 50 wt % methylcyclopentane, from about 5 wt % to about 50 wt % cyclohexane and/or from about 10 wt % to about 80 wt % benzene. The benzene fraction is recycled to the hydroalkylation reaction, whereas the methylcyclopentane-rich fraction may be recovered for use as a motor gasoline blendstock.

In another embodiment, the fractionation of the hydroalkylation reaction effluent produces at least two $C_6$ fractions, namely a first, methylcyclopentane containing fraction and a second, benzene-containing fraction. The first fraction typically comprises from about 1 wt % to about 10 wt % of the liquid hydroalkylation reaction effluent and contains from about 1 wt % to about 99 wt %, such as from about 2 wt % to about 80 wt %, of the methylcyclopentane contained in hydroalkylation reaction effluent. Thus the first fraction generally contains from about 5 wt % to about 50 wt % methylcyclopentane, together with about 5 wt % to about 50 wt % cyclohexane and about 10 wt % to about 80 wt % benzene. The second fraction typically comprises from about 90 wt % to about 99 wt % of the liquid hydroalkylation effluent and contains up to 5 wt %, such as from about 0.01 wt % to about 1 wt %, methylcyclopentane, possibly no detectable methylcyclopentane, the reminder being composed mainly of benzene and cyclohexane. The second fraction is therefore subjected to the dehydrogenation reaction discussed above, while the first fraction may be recovered for use as a motor gasoline blendstock.

As discussed above, fractionation of the hydroalkylation reaction effluent also produces a $C_{12}$ fraction containing most of the cyclohexylbenzene and a $C_{18}$ fraction containing most of the dicyclohexylbenzene. The cyclohexylbenzene is fed to the oxidation step discussed below whereas, depending on the amount of the dicyclohexylbenzene produced, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia and mixtures thereof. Generally, the acid catalyst includes at least one aluminosilicate, aluminophosphate or silicoaluminphosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

It is to be appreciated that the transalkylation and dealkylation reactions can, and typically will generate additional methylcyclopentane, and hence the products of these reactions, conveniently in admixture with all or a portion of the hydroalkylation product, can be subjected to the separation steps described above to generate the $C_6$ fraction(s), which may subsequently be subjected to dehydrogenation.

Cyclohexylbenzene Oxidation

In order to convert the cyclohexylbenzene into phenol and cyclohexanone, the cyclohexylbenzene is oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N', N"-trihydroxyisocyanuric acid is employed in an amount between 0.0001 wt % to 15 wt %, such as between 0.001 wt % to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent may be subjected to a cleavage reaction, with or without undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other absorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other absorbable components, and provide an oxidation composition reduced in oxidation catalyst or other absorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

Another step in the conversion of the cyclohexylbenzene into phenol and cyclohexanone involves the acid-catalyzed cleavage of the cyclohexyl-1-phenyl-1-hydroperoxide produced in the oxidation step.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm and to no greater than 3000 wppm, or at least 150 wppm and no greater than 2000 wppm of the acid catalyst, or at least 300 wppm and no greater than 1500 wppm of the acid catalyst, based upon total weight of the cleavage reaction mixture.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12 and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage reaction mixture may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam and nylons, such as nylon 6 and nylon 6,6.

The phenol produced through the processes disclosed herein may be used, for example, to produce phenolic resins, bisphenol A, ε-caprolactam, adipic acid and/or plasticizers.

Description According to the Figures

The invention will now be more particularly described with reference to the accompanying drawings and the following non-limiting examples.

Figure 1:
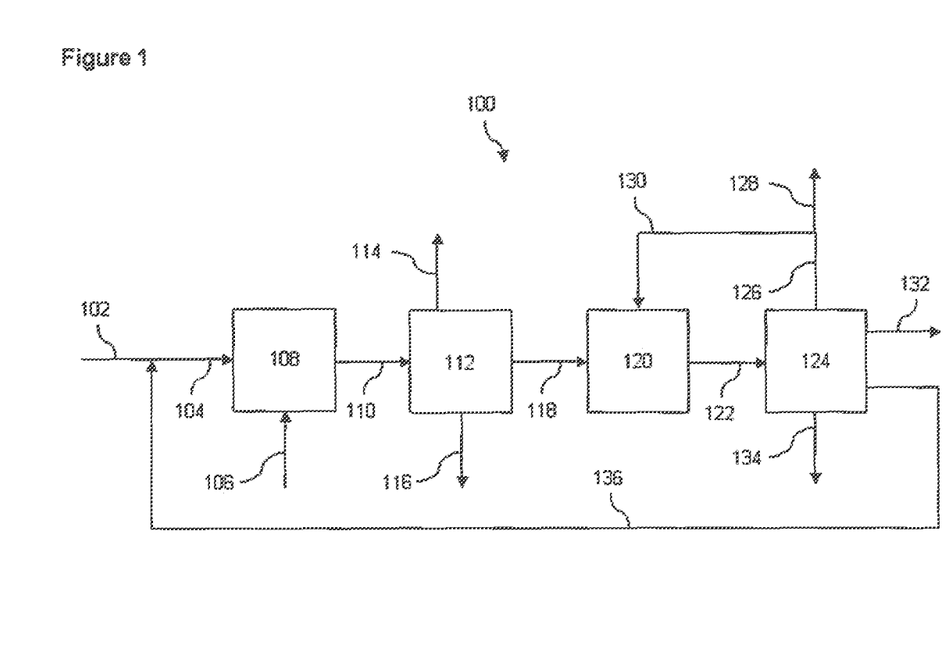
FIG. 1 is a schematic diagram of a process for producing cyclohexylbenzene according to a first embodiment of the invention.

Referring to FIG. 1, a process 100 is shown for producing cyclohexylbenzene according to a first embodiment of the invention. In the process 100, fresh, make-up benzene in line 102 is combined with recycle benzene provided from a portion of the second effluent stream in line 136, creating a combined fresh and recycle benzene stream in line 104. The combined benzene stream in line 104, along with a hydrogen stream in line 106, are provided to hydroalkylation reactor system 108, where they are contacted with a first catalyst under hydroalkylation conditions sufficient to form a first effluent stream in line 110.

The first effluent stream in line 110 comprises cyclohexylbenzene, cyclohexane, methylcyclopentane, unreacted benzene and unreacted hydrogen, and is passed to a first separation system 112. In first separation system 112, the first effluent stream is separated into a stream comprising mainly hydrogen in line 114, a stream comprising mainly cyclohexylbenzene in line 116, and a stream comprising mainly $C_6$ hydrocarbons, such as benzene, cyclohexane and methylcyclopentane in line 118.

The stream comprising mainly $C_6$ hydrocarbons in line 118 is provided along with a recycle hydrogen stream in line 130 to dehydrogenation reactor system 120, where they may be contacted with a second catalyst (i.e., a dehydrogenation catalyst) under dehydrogenation conditions sufficient to convert at least a portion of the cyclohexane to benzene and form a second effluent stream in line 122. In dehydrogenation reactor system 120, the activity for affecting methycyclopentane concentration is low, and the amount of methylcyclopentane in the second effluent stream in line 122 changes by no more than 10%, such as by no more than 2.0%, of the amount of the total stream comprising mainly $C_6$ hydrocarbons in line 118.

The second effluent stream in line 122 is passed to a second separation system 124, where the second effluent stream is separated into a stream comprising mainly hydrogen in line 126. A portion of the stream comprising mainly hydrogen in line 126 is taken as a product hydrogen stream in line 128 and may be used for other purposes in the process 100, for example, as hydrogen for the hydroalkylation reactor system 108. The remaining portion of the stream comprising mainly hydrogen in line 126 is taken as the aforementioned recycle hydrogen stream in line 130.

Also in second separation system 124, the second effluent stream is further separated into a methylcyclopentane rich stream in line 132 and the aforementioned recycle benzene stream in line 136, which closes the hydroalkylation-dehydrogenation circuit. The methylcyclopentane rich stream may recovered for use as a fuel, or for sale as a high octane motor gasoline blending stream. In this manner, methylcyclopentane is removed from the hydroalkylation-dehydrogenation circuit to prevent excessive build-up of that unreactive component.

Further in the second separation system 124, the second effluent stream is separated into a stream containing toluene and components of lower volatility in line 134, and again used, for example, as fuel or sold as a high octane motor gasoline blending stream. Conveniently there is a low amount of benzene in the stream containing toluene and components of lower volatility in line 134, say, less than 1 wt %.

Figure 2:
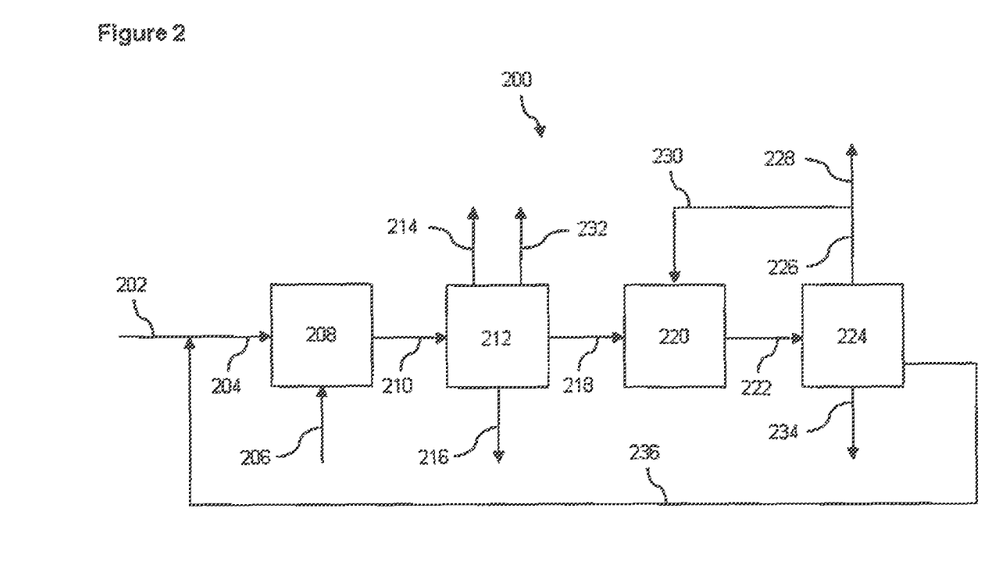
FIG. 2 is a schematic diagram of a process for producing cyclohexylbenzene according to a second embodiment of the invention.

Referring to FIG. 2, a process 200 is shown for producing cyclohexylbenzene according to a second embodiment of the invention. In the process 200, fresh, make-up benzene in line 202 is combined with recycle benzene provided from a portion of the second effluent stream in line 236, creating a combined fresh and recycle benzene stream in line 204. The combined benzene stream in line 204, along with a hydrogen stream in line 206, are provided to hydroalkylation reactor system 208, where they are contacted with a first catalyst under hydroalkylation conditions sufficient to form a first effluent stream in line 210.

The first effluent stream in line 210 comprises cyclohexylbenzene, cyclohexane, methylcyclopentane, unreacted benzene and unreacted hydrogen, and is passed to a first separation system 212. In first separation system 212, the first effluent stream is separated into a stream comprising mainly hydrogen in line 214, a stream comprising mainly cyclohexylbenzene in line 216, and first and second streams comprising mainly $C_6$ hydrocarbons in lines 218 and 232, respectively. The first $C_6$ stream in line 218 comprises benzene, cyclohexane and optionally some methylcyclopentane, whereas the second $C_6$ stream in line 232 is rich in methylcyclopentane, which can be removed from the process 200 for use as a fuel or for sale as a high octane motor gasoline blending stream. In this manner, methylcyclopentane is removed from the hydroalkylation-dehydrogenation circuit to prevent excessive build-up of that unreactive component.

The first $C_6$ stream in line 218 is provided along with a recycle hydrogen stream in line 230 to dehydrogenation reactor system 220, where they are contacted with a dehydrogenation catalyst under dehydrogenation conditions sufficient to convert at least a portion of the cyclohexane to benzene and form a second effluent stream in line 222. In the dehydrogenation reactor system 220, the activity for affecting methycyclopentane concentration is low, and the amount of methylcyclopentane in the second effluent stream in line 222 changes by no more than 2.0% of the amount of the total stream comprising mainly $C_6$ hydrocarbons in line 218.

The second effluent stream in line 222 is passed to a second separation system 224, where the second effluent stream is separated into a stream comprising mainly hydrogen in line 226, a stream containing toluene and components of lower volatility in line 234 and the recycle benzene stream in line 236. A portion of the stream comprising mainly hydrogen in line 126 is taken as a product hydrogen stream in line 228 and may be used for other purposes in the process 200, for example, as hydrogen for the hydroalkylation reactor system 208. The remaining portion of the stream comprising mainly hydrogen in line 126 is taken as the aforementioned recycle hydrogen stream in line 230. The toluene-containing stream in line 234 typically contains only a small amount of benzene, say, less than 1 wt %, and can also be used as fuel or sold as a high octane motor gasoline blending stream.

EXAMPLE 1

Figure 3:
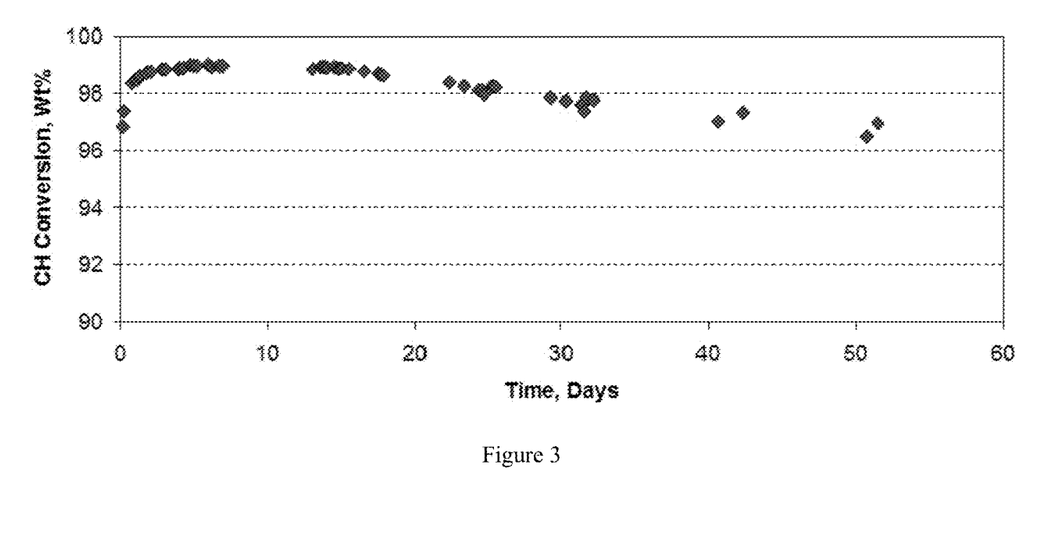
FIG. 3 is a graph showing the conversion of cyclohexane (CH) over time in the dehydrogenation process of Example 1.
Figure 4:
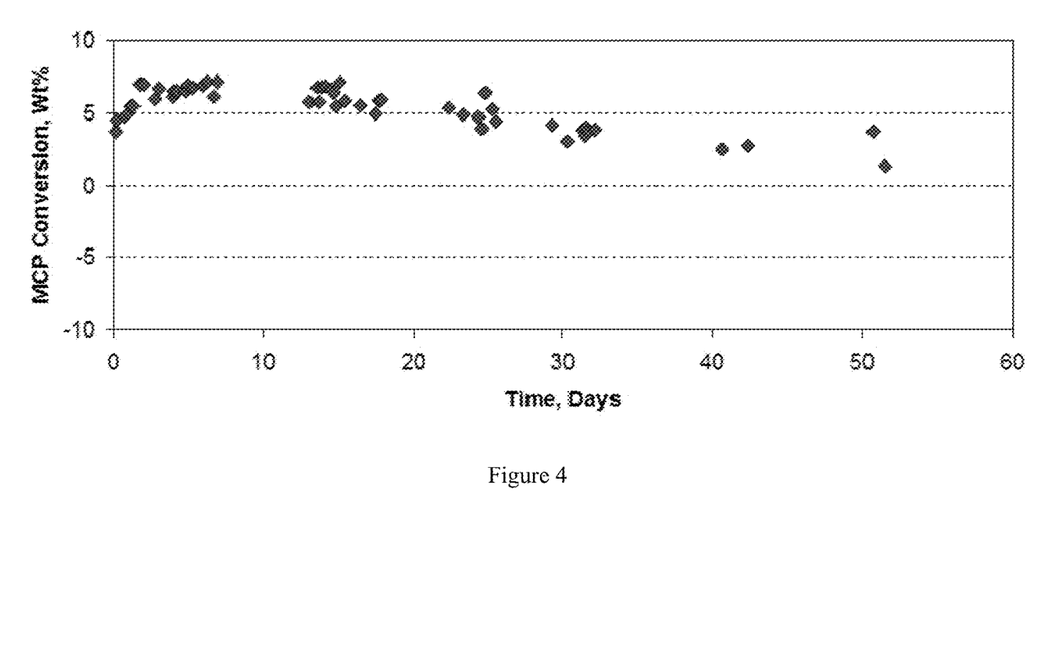
FIG. 4 is a graph showing the conversion of methylcyclopentane (MCP) over time in the dehydrogenation process of Example 1.
Figure 5:
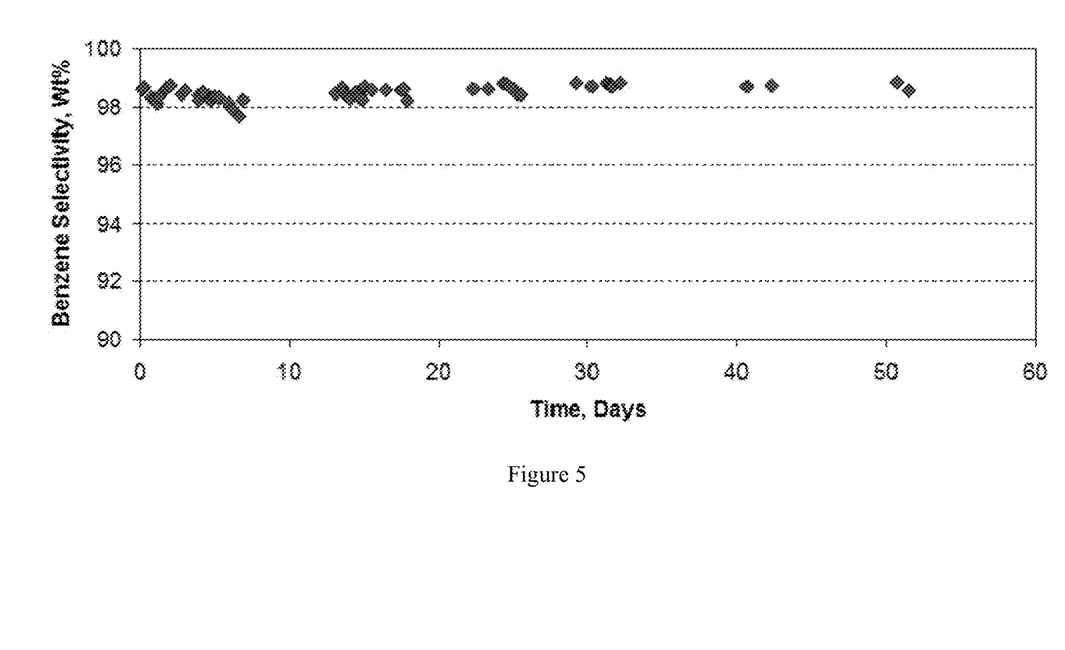
FIG. 5 is a graph showing the selectivity to benzene of the converted cyclohexane over time in the dehydrogenation process of Example 1.

A dehydrogenation catalyst comprising 1 wt % platinum and 0.15 wt % tin on a silicon oxide support was crushed to 60/100 mesh and loaded into ½" (1.27 cm) outer diameter (OD) tubular downflow reactor. The catalyst was then contacted with a feed composition (simulating a portion of first effluent stream) comprising 89 wt % benzene, 10 wt % cyclohexane and 1 wt % methylcyclopentane under dehydrogenation conditions of 480° C., 0.689 MPag, 10 hr$^{-1}$ weight hourly space velocity (WHSV), and a molar ratio of hydrogen to hydrocarbon (H2/HC) of 4. The dehydrogenation reaction was maintained in this fashion for over 50 days of continuous operation, with the dehydrogenation product (second effluent stream) flashed at ambient temperature (about 25° C.), and the liquid fraction analyzed from time to time on an Agilent 5690 Gas Chromatograph using a DB-1 column. The results are summarized in FIGS. 3 to 5 wherein.

Also present in the dehydrogenation product were minor amounts of methane, propane, isomers of butane, isomers of methylpentane, n-hexane, methylcyclopentene, cyclohexene, toluene, isomers of xylene and biphenyl (about 0.0004 wt % to 0.08 wt % of any given component).

EXAMPLE 2

Following the long experiment of Example 1 (i.e., beginning about day 53), using the same dehydrogenation catalyst on the same apparatus with the same feed composition and experimental protocol, dehydrogenation conditions were varied over the course of several days. The results are recorded in Table 1, which demonstrate, among other things, the very low level of activity of dehydrogenation catalyst and conditions for affecting methylcyclopentane. Negative MCP conversion entries indicate an increase in the amount of methylcyclopentane in the dehydrogenation product (second effluent stream) relative to the feed composition (simulating a portion of first effluent stream), which is possible at certain dehydrogenation conditions, particularly lower temperatures. This implies the acidity of the catalyst is low enough to prevent methylcyclopentane destruction to acyclic paraffins, but that some acidity may be present to enable a minor amount of isomerization of cyclohexane.

TABLE 1

| | | | |
|---|---|---|---|
| Total Pressure (MPag) | 0.689 | 0.896 | 0.710 |
| Molar ratio of hydrogen to hydrocarbon (H2/HC) (mol/mol) | 4 | 4 | 2 |
| Temperature (° C.) | 420 | 420 | 460 |
| Weight Hourly Space Velocity (WHSV) (hr$^{-1}$) | 7.5 | 7.5 | 10.0 |
| Cyclohexane Conversion (%) | 47.1 | 31.6 | 96.8 |
| Methylcyclopentane Conversion (%) | −1.3 | 1.1 | −5.8 |
| Benzene Selectivity (%) | 97.5 | 97.0 | 98.0 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing cyclohexylbenzene, the process comprising:
    (a) contacting benzene and hydrogen under hydroalkylation conditions effective to form a first effluent stream comprising cyclohexylbenzene, cyclohexane, methylcyclopentane, and unreacted benzene;
    (b) separating at least a portion of the first effluent stream into (i) a $C_6$-rich stream comprising benzene and cyclohexane and (ii) a cyclohexylbenzene-rich stream;
    (c) contacting at least a portion of the $C_6$-rich stream with a dehydrogenation catalyst under dehydrogenation conditions to convert at least 90 wt % of the cyclohexane to benzene thereby forming a second effluent, wherein an amount of methylcyclopentane in the second effluent differs from an amount of methylcyclopentane in the portion of the $C_6$-rich stream by no more than 5 wt %, where the amount of methylcyclopentane in the portion of the $C_6$-rich stream is on the basis of total weight of the portion of the $C_6$-rich stream, and the amount of methylcyclopentane in the second effluent stream is on the basis of the total weight of the second effluent stream;
    (d) recovering a methylcyclopentane-rich stream from the first effluent stream or the second effluent stream, wherein the methylcyclopentane-rich stream comprises from about 5 wt % to about 50 wt % methylcyclopentane, wherein the wt % is based upon the weight of the methylcyclopentane-rich stream and the recovered methylcyclopentane-rich stream is a motor gasoline blendstock;
    (e) separating at least a portion of the second effluent stream into a benzene recycle stream; and
    (f) recycling at least a portion of the benzene recycle stream to the contacting step (a).

2. The process of claim 1, wherein the amount of methylcyclopentane in the second effluent differs from the amount of methylcyclopentane in the portion of the $C_6$-rich stream by no more than 2 wt %.

3. The process of claim 1, wherein the cyclohexylbenzene-rich stream is recovered from said first effluent stream by fractionation.

4. The process of claim 1, wherein the contacting step (a) is conducted in the presence of a hydroalkylation catalyst comprising a molecular sieve of the MCM-22 family and a hydrogenation metal.

5. The process of claim 1, wherein the dehydrogenation catalyst comprises 0.05 wt % to 0.5 wt % of a metal selected from Group 14 of the Periodic Table of Elements; and 0.1 wt % to 2 wt % of a metal selected from Groups 6 to 10 of the Periodic Table of Elements, the wt % s being based upon total weight of the dehydrogenation catalyst.

6. The process of claim 5, wherein the metal selected from Group 14 of the Periodic Table of Elements comprises tin.

7. The process of claim 5, wherein the metal selected from Groups 6 to 10 of the Periodic Table of Elements comprises platinum and/or palladium.

8. The process of claim 1, wherein the dehydrogenation conditions comprise a temperature between 200° C. and 550° C. and a pressure between 100 kPa and 7,000 kPa, gauge.

9. The process of claim 1, wherein the methylcyclopentane-rich stream is removed from either the first or the second effluent stream by fractionation.

10. The process of claim 1, wherein the methylcyclopentane-rich stream contains from about 5 wt % to about 50 wt % cyclohexane, the wt % based upon the weight of methylcyclopentane-rich stream.

11. The process of claim 1, wherein the methylcyclopentane-rich stream contains from about 10 wt % to about 80 wt % benzene, the wt % based upon the weight of the methylcyclopentane-rich stream.

12. The process of claim 1, wherein the portion of the benzene recycle stream that is recycled to the contacting step (a) contains from about 0.1 wt % to about 5 wt % methylcyclopentane, the wt % based upon the weight of the portion of the benzene recycle stream.

13. The process of claim 1, wherein the portion of the benzene recycle stream that is recycled to the contacting step (a) contains from about 0.1 wt % to about 1 wt % methylcyclopentane, the wt % based upon the weight of the portion of the benzene recycle stream.

14. The process of claim 1, wherein the portion of the benzene recycle stream that is recycled to the contacting step (a) contains from about 0.1 wt % to about 10 wt % methylcyclopentane, the wt % based upon the weight of the portion of the benzene recycle stream.

\* \* \* \* \*